Figure 1:
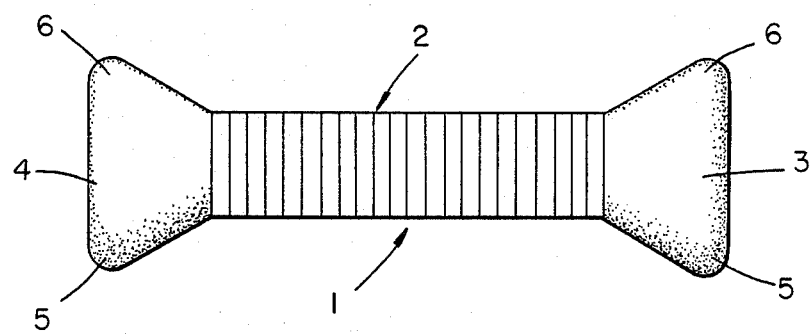

United States Patent [19]

York

[11] Patent Number: 4,778,457
[45] Date of Patent: Oct. 18, 1988

[54] DISPOSABLE APPLICATOR

[76] Inventor: Kenneth K. York, 2300 N. Edgement St., Los Angeles, Calif. 90027

[21] Appl. No.: 927,929

[22] Filed: Nov. 6, 1986

[51] Int. Cl.⁴ .............................................. A61M 35/00
[52] U.S. Cl. ..................... 604/290; 604/289; 604/294; 604/1; 128/355
[58] Field of Search ............... 604/289–290, 604/294, 1–3; 128/355, 357

[56]  References Cited
U.S. PATENT DOCUMENTS

| 3,075,527 | 1/1963 | Bechtold . | |
| 3,508,547 | 4/1970 | Deuschle | 604/1 |
| 3,910,284 | 10/1975 | Orentreich | 128/355 |
| 4,140,409 | 2/1979 | DeVries . | |
| 4,259,955 | 4/1981 | Ritter | 604/1 |
| 4,291,697 | 9/1981 | Georgevich . | |
| 4,459,987 | 7/1984 | Pangburn | 128/355 |
| 4,540,408 | 9/1985 | Lloyd . | |

OTHER PUBLICATIONS

*Pye's Surgical Handicraft*, by Hamilton Bailey, ed., The Williams & Williams Co., Baltimore, 1950, pp. 496–501.

Primary Examiner—Dalton L. Truluck
Assistant Examiner—Denise Whelton
Attorney, Agent, or Firm—Kendrick, Lorig & Bright

[57]  ABSTRACT

A disposable applicator for treating blepharitis in the human eye includes a handle having at least one mildly abrasive, porous sponge impregnated with at least one antimicrobial agent or antimicrobial agent combined with a soap or detergent such as an antibiotic or PVP-I.

4 Claims, 1 Drawing Sheet

DISPOSABLE APPLICATOR

This invention relates to a disposable mildly abrasive applicator for applying one or more ocularly biocompatible, antimicrobial agents or an antimicrobial agent combined with a detergent or soap to the eyelid of an eye in a human or an animal and simultaneously exfoliate the skin, remove surface debris and clean and/or kill bacteria that cause blepharitis. Examples of such antimicrobial agents are antibiotics, polyvinylpyrrolidone-iodine (PVP-I), antiseptic soap (such as green soap), hexachlorophene, fungicides, etc. PVP-I scrub solution is an example of a combination antimicrobial agent and soap. The applicator itself includes a handle for holding the applicator, preferably at the fingertips, and one or more antimicrobial agent-applying means. The antimicrobial agent-supplying means is preferably an absorbent coherent, mildly abrasive member, such as a sponge or brush, having a shape complementary to the rim of the human eyelid. In preferred embodiments, the antimicrobial agent-applying means is a mildly abrasive, porous sponge impregnated with one or more antimicrobial agents such as PVP-I.

The invention can be better understood by reference to the accompanying drawing, which illustrates the preferred embodiment of the new disposable applicator.

The drawing shows a disposable applicator 1 having a handle 2 that facilitates holding applicator 1 between two fingers. At opposite ends of handle 2 are porous sponges 3 and 4. Each of sponges 3 and 4 is mildly abrasive, and is impregnated with at least one antimicrobial agent such as an antibiotic of PVP-I. Sponge members 3 and 4 are sufficiently abrasive to open the meibomian glands and to remove exfoliated skin. Each of sponges 3 and 4 may have a frustoconical shape with softly rounded corners such as corners 5 and 6. This shape is complementary to the rim of the human eyelid, and facilitates the simultaneous, one-step application of the antimicrobial agent or an antimicrobial agent combined with a soap or detergent and the desirable abrading to open the meibomian glands and to remove exfoliated skin.

What is claimed is:

1. A method for treating blepharitis on a human eyelid without damaging the eyelid or other eye tissues comprising abrading the rim of said eyelid sufficiently to open the meibomian glands of said eyelid and to remove exfoliated skin from said eyelid without damaging said eyelid or surrounding eye tissues and, simultaneously, applying at least one antimicrobial agent or at least one antimicrobial agent combined with a soap or detergent in an amount sufficient to clean said eyelid and to kill bacteria that cause blepharitis on said eyelid, utilizing, for said simultaneous abrading and applying, a mildly abrasive applicator including at least one antimicrobial agent-applying means that is sufficiently abrasive to open the meibomian glands and to remove exfoliated skin from said eyelid.

2. The method of claim 1 further comprising using a mildly abrasive porous sponge or brush in said abrading step.

3. A method for treating blepharitis on a human eyelid without damaging the eyelid or other eye tissues comprising abrading the rim of said eyelid sufficiently to open the meibomian glands of said eyelid and to remove exfoliated skin from said eyelid without damaging said eyelid or surrounding eye tissues and, simultaneously, applying at least one antimicrobial agent or at least one antimicrobial agent combined with a soap or detergent in an amount sufficient to clean said eyelid and to kill bacteria that cause blepharitis on said eyelid, utilizing, for said simultaneous abrading and applying, a mildly abrasive disposable applicator including at least one antimicrobial agent-applying means that is sufficiently abrasive to open the meibomian glands and to remove exfoliated skin from said eyelid.

4. The method of claim 3 comprising utilizing, as said mildly abrasive, disposable applicator, an applicator comprising a mildly abrasive porous sponge or brush.

* * * * *